United States Patent [19]

Kochansky et al.

[11] Patent Number: 6,037,374
[45] Date of Patent: Mar. 14, 2000

[54] COMPOSITION AND METHOD FOR THE CONTROL OF PARASITIC MITES IN HONEY BEES

[75] Inventors: Jan P. Kochansky, Adelphi; Hachiro Shimanuki, Laurel; Mark Francis Feldlaufer, Annapolis; Jeffery S. Pettis, Glenelg, all of Md.

[73] Assignee: The United States of America as represented by the Secretary of Agriculture, Washington, D.C.

[21] Appl. No.: 08/974,709

[22] Filed: Nov. 19, 1997

[51] Int. Cl.⁷ .......................... A01N 37/02; A01N 25/04
[52] U.S. Cl. .................. 514/557; 514/770; 514/772; 514/772.6; 514/784; 514/944; 514/964; 424/405; 424/484; 424/486; 424/487
[58] Field of Search ...................... 514/557, 770, 514/772.6, 944, 964, 772, 784; 424/405, 484, 487, 486

[56] References Cited

U.S. PATENT DOCUMENTS

| | | | |
|---|---|---|---|
| 3,635,836 | 1/1972 | Mullen | 516/103 |
| 3,652,420 | 3/1972 | Hill | 510/116 |
| 4,581,042 | 4/1986 | Willmore | 51/293 |
| 4,927,813 | 5/1990 | Bernstein | 514/65 |
| 5,645,845 | 7/1997 | Neumann et al. | 424/405 |

OTHER PUBLICATIONS

Clark, Kerry J., "Application of formic acid liquid or gel for the control of Honey Bee tracheal mites," Canadian Beekeeping, vol. 17(4), 1992, pp. 86–89.

Zweig, G., "Environmental Aspects of controlled Release Pesticide formulations" in "Controlled Release Pesticides," Scher. H.B. (Ed.), ACS Symposium Series 53, American Chemical Society, Washington, DC, 1977, pp. 44–46.

WPIDS Abstract, Accession No. 79–64030B (1979).

Rafiq Ahmad, *Pakistan J. Zool.*, vol. 23(4), pp. 363–364, 1991.

Nelson et al., *Bee Science*, vol. 3(3), pp. 128–134, 1994.

Nassenheider Evaporator Specifications, Manufactured in Germany, 1994.

*Primary Examiner*—John Pak
*Attorney, Agent, or Firm*—M. Howard Silverstein; John D. Fado; Janelle S. Graeter

[57] ABSTRACT

Gel compositions of formic acid and a gelling agent such as fumed silica or polyacrylic acid have been prepared for controlling parasitic mites of honey bees. The gels provide slow-release capability and have been found effective against both *Varroa jacobsoni* and *Acarapis woodi*. They are advantageous in that they have improved handling characteristics and are safer than liquid formic acid, which is quite corrosive.

22 Claims, 2 Drawing Sheets

COMPOSITION AND METHOD FOR THE CONTROL OF PARASITIC MITES IN HONEY BEES

BACKGROUND OF THE INVENTION

1. Field of the Invention

Parasitic mites are serious pests affecting honey bee populations worldwide. Both *Varroa jacobsoni* and the tracheal mite *Acarapis woodi* have been identified as the cause of infestations resulting in an extensive reduction in honey bee populations. This population reduction has had serious consequences in agriculture, since honey bees are critical to pollination in the fields and thus to the successful production of many crops. Although various treatments have been attempted, many have been unsuccessful due in large part to the toxicity of the chemicals utilized or to difficulties in registration with environmental agencies. Only one product is currently registered in the United States for control of Varroa: Apistan® (Wellmark International, Dallas, Tex.), a plastic strip containing fluvalinate. Tracheal mites can be controlled with menthol or, less effectively, by use of vegetable oil patties placed in the hive. None of these materials is active against both parasitic mites, however, and the use of only a single registered product is conducive to the development of resistance. There has thus been a strong incentive to develop a product which will provide safe and effective protection for honey bees over existing treatments.

2. Description of the Related Art

Formic acid has been used in liquid form in Europe and Canada and has been shown to control parasitic mites of honey bees in a wide variety of situations. The first comprehensive report on such use of formic acid appeared in a special issue on varroatosis (Ritter and Ruttner. 1980. *Allg. Dtsch. Imkerztg.* vol. 14, pp. 151–155). Subsequently, the "Illertisser Mite plate" (IMP), a cardboard-like material that could be soaked with formic acid and placed in the hive was developed (Wachendörfer et al. 1985. *Apidologie.* vol. 16, pp. 291–305). This method, or modifications of it, was tested against parasitic bee mites in a number of countries, including Germany (Hoppe et al. 1989. *Amer. Bee J.* vol 129, pp. 739–742), Sweden (Fries, I. 1989. *Swedish J. Agric. Res.* vol. 19, pp. 213–216) and Dubai (Bracey and Fisher. 1989. *Amer. Bee J.* vol. 129, pp. 735–737) Other known application methods have included soaked cheesecloth (Liu and Nasr. 1992. *Amer. Bee J.* vol. 132, pp. 666–668) and containers with wicks (Sharma et al. 1983. *Indian Bee J.* vol. 45, pp. 1–2; Lupo and Gerling. 1990. *Apidologie.* vol. 21, pp. 261–267). Nelson et al. (1994. *Bee Science.* vol. 3, no. 3, pp. 129–134) disclosed formic acid application for controlling tracheal mites and compared treatments using liquid formic acid, formic acid gel-strips, menthol-paste and the German product IMP. Most of these methods use varying concentrations of dilute liquid formic acid, and most require multiple applications. In addition, use of the IMP apparatus necessitates the removal of part of the honeycomb from the hive to meet space requirements.

Formic acid is very corrosive and dispensing it inside the beehive has been problematic. The current methods require handling liquid formic acid, frequent applications and/or extensive hive manipulation. Due to its hazardous nature, the development of a formic acid formulation that was both safer than a liquid and had the advantage of fewer applications was desirable.

Furthermore, an increase in resistance by Varroa to the fluvalinate-containing control product over several years in Europe, and the expectation that such resistance is inevitable elsewhere, has provided an additional incentive for the development of a useful formic acid formulation. By having an additional effective treatment available and the capability of alternating treatments, such resistance can at least be delayed and possibly avoided altogether.

SUMMARY OF THE INVENTION

We have discovered a gel formulation of formic acid and a delivery system which is effective for the control of parasitic mites of honey bees.

In accordance with this discovery, it is an object of the invention to provide a gel composition comprising formic acid in an amount effective for controlling parasitic mites of honey bees and a gelling agent.

It is also an object of the invention to provide a dispenser useful for the treatment of parasitic mites of honey bees containing the novel gel composition.

It is a further object of the invention to provide a method of controlling parasitic mites of honey bees using the formic acid composition.

Other objects and advantages of the invention will become readily apparent from the following description.

DETAILED DESCRIPTION OF THE INVENTION

Figure 1:
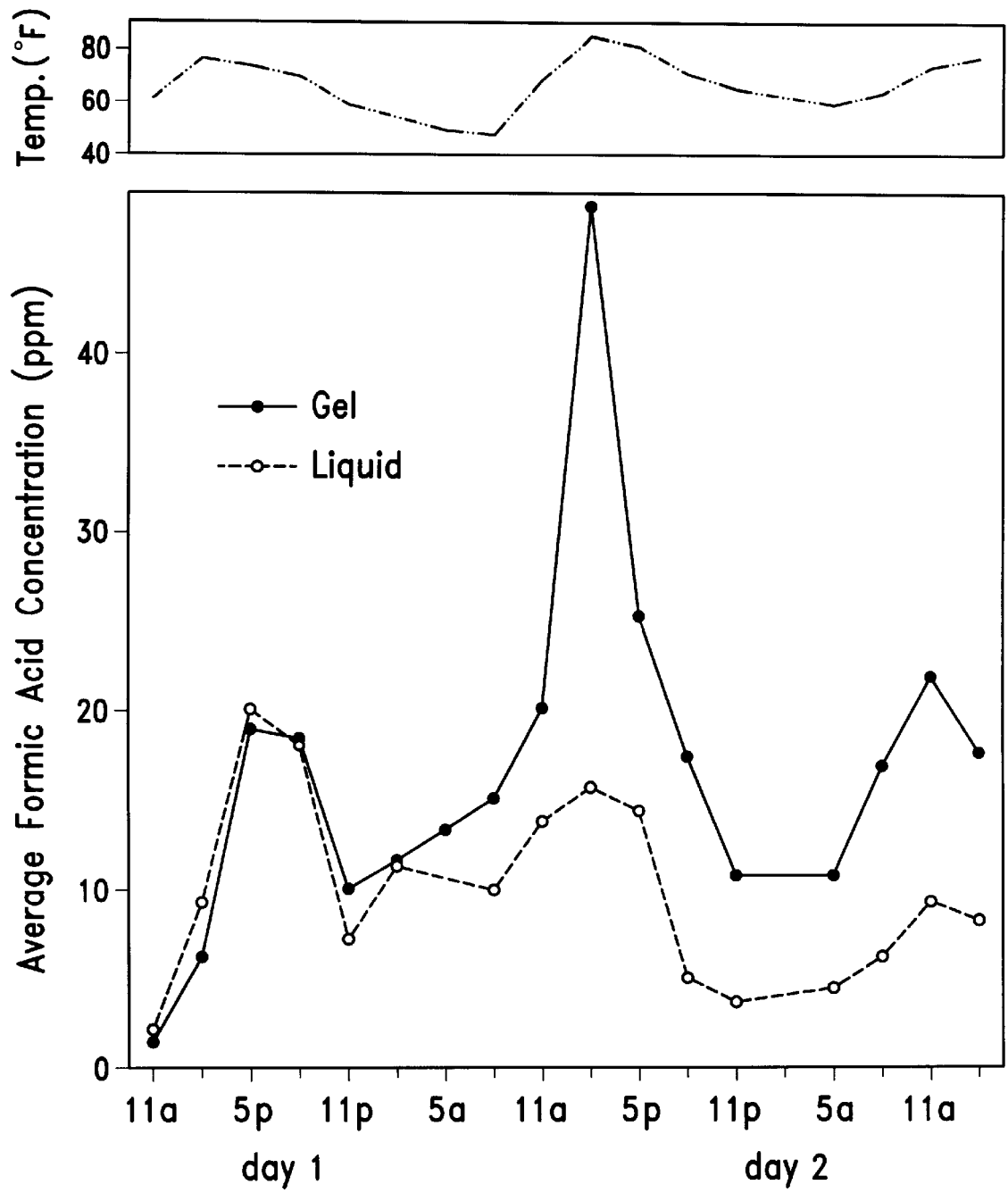
FIG. 1 shows the comparison of formic acid levels in colonies treated with gel packets (●) or liquid (○). Formic acid levels (ppm) were determined inside colonies using Dräger air monitoring tubes. Gel packets and liquid applications were initiated at 10 AM on day 1. Levels represent the average reading in three colonies for each treatment. Ambient temperatures are shown in the top box.

The novel gel formulation of formic acid has significant advantages over liquid formic acid applications. Gels require no dilution and have improved handling characteristics, thereby reducing the hazards associated with handling liquid formic acid which is quite corrosive and spills and splashes easily. The gel also acts as a slow release agent, thus reducing the number of applications necessary to achieve adequate control.

The gel composition comprises formic acid and a gelling agent. Useful gelling agents are fumed silica or polyacrylic acid, preferably high molecular weight polyacrylic acids. Formic acid, as well as the gelling agents, are widely available commercially and are approved by regulatory agencies for food additive, food contact or pharmaceutical use. Fumed silica (or silicon dioxide) is produced by a flame hydrolysis process and is characterized by exceedingly particles (i.e. about 7 to about 14 nm in size). Commercial examples of useful fumed silicas are Cab-O-Sil® (Cabot Corp., Boston, Mass.), Aerosil® (Degussa Corp., Ridgefield Park, N.J.) and HDK® fumed silica (Wacker Silicones Corp., Adrian, Mich.). The untreated, hydrophilic grades of fumed silica (for example, Cab-O-Sil® M-5 and EH-5) are suitable, but the silanized, hydrophobic grades are not, since they are not wetted by the formic acid. High molecular weight polyacrylic acids may range in molecular weight from about 450,000 to about 4 million, and also may vary in degree of cross-linking. Commercial examples are the Carbopol® series (B.F. Goodrich, Cleveland, Ohio). Selection of certain grades from these two classes is not to be construed as exclusion of other suitable grades or manufacturers.

In a composition containing formic acid and fumed silica, varying concentrations of formic acid were tested for acceptable gel properties. It was found that as the amount of formic acid increased, the amount of fumed silica required to achieve an acceptable gel consistency decreased (see Table I). High molecular weight polyacrylic acids were also tested as gelling agents. Carbopol® 934 and 941 (B.F. Goodrich, supra) were tested with varying concentrations of formic acid. Results are shown in

TABLE I

Gels containing Formic Acid and Fumed Silica in Varying Amounts.

| % Formic acid (v/v) in water | % Fumed silica[1] | Gel properties |
| --- | --- | --- |
| 0 | 15% | initially acceptable but degraded over time to a mobile slurry |
| 25 | 10 | acceptable |
| 45 | 8.5 | acceptable |
| 65 | 7 | acceptable |
| 90 | <7 | acceptable |

[1]Grams/100 grams formic acid solution

Table II and indicate that acceptable gels may be obtained at lower formic acid concentrations. At concentrations above about 75%, however, gelling capability falls off rapidly. The solution becomes difficult to mix with the formation of gummy lumps.

TABLE II

Gels Comprising High Molecular Weight Polyacrylates at Varying Concentrations of Formic Acid.

| % Formic acid (v/v) in water | 5% Carbopol 934 | 5% Carbopol 941 |
| --- | --- | --- |
| 25 | acceptable | acceptable |
| 45 | acceptable | acceptable |
| 65 | acceptable | acceptable |
| 75 | acceptable | acceptable |
| 85 | white mobile slurry | viscous lumpy liquid |
| 90 | colorless liquid with white sediment, no apparent thickening | colorless liquid with white sediment, no apparent thickening |

Various other substances were tested but did not provide acceptable gels. For example, some polyacrylamide gellants produced a leathery solid or a thick rubbery material at high concentrations (Nelson et al., supra) which does not work well and is much harder to mix, requiring close control of mixing time and conditions before the material becomes too thick to handle. Other gellants or lower concentrations resulted in viscous liquids approximately the consistency of honey with no thixotropic properties. In addition, emulsions of unspecified compositions as well as treated and untreated bentonite clays were tested but gave little or no thickening of 65% formic acid. Vegetable-derived gellants such as agar and guar gum were destroyed by the formic acid.

Gels are prepared by combining formic acid with gelling agent and mixing until homogeneous and of desired consistency. Before combining, formic acid is generally diluted to a use concentration of about 70% (v/v) in water. Formic acid concentrations may vary considerably, however the preferred concentration is about 65%. Although both lower and higher ranges have been found effective, a note of caution should be taken in the higher ranges since formic acid is toxic and may be detrimental to the health of the honey bees. The amount of gelling agent may vary also, as illustrated in both Table I and Table II, and is not critical so long as the proper consistency is achieved.

An acceptable gel is soft but thixotropic and non-slumping, with a consistency ranging from pudding-like to that of caulking compound. Fumed silicas are more easily handled than polyacrylic acids, requiring only brief agitation to achieve a satisfactory gel. In addition, fumed silicas are insoluble in formic acid and thus form a well-dispersed solid phase. The rate of evaporation of the formic acid therefore does not change greatly with time. Polyacrylic acids require several hours to disperse and should be added to well-agitated formic acid in order to avoid the formation of lumps which persist for a long time once they are formed. In addition, the polyacrylic acids dissolve in formic acid, therefore the viscosity of the composition increases rapidly with evaporation of the formic acid, reducing the rate of evaporation as the quantity of remaining acid decreases.

The gel can be used in various types of dispensers which allow emission of formic acid vapor. Perforated containers are useful, whether pre-perforated with some mechanism for uncovering the perforations or perforated by various means just before use. The containers may be placed in several locations within the hive such that the vapors are distributed in the hive. The gel may also be applied directly, for example with a caulking gun.

The gel may be left in the hive until the formic acid evaporates, however, the treatment is most effective if carried out over a complete brood cycle. In general, the gel packets described in the examples are effective over about a 21-day period, which is a sufficient amount of time to encompass the brood cycle.

The following examples are intended to illustrate the invention and are not intended to limit the scope of the invention as defined by the claims.

EXAMPLES

Example 1

Preparation of gel packets.

Gel was prepared by diluting formic acid to 65–70% (v/v) in water. Fumed silica was added to the formic acid at a ratio of 7 g per 100 g formic acid solution and mixed until homogeneous and of the desired consistency.

Gel packets were prepared by introducing 200 g of a 65% formic acid gel into polyethylene bags that were then heat-sealed to form a packet with final dimensions of approximately 6"×6"×3/8". This size could easily be laid over the top bars of the upper brood chamber and not interfere with hive closure. Prior to the replacement of the inner cover, four slits were made in the top side of the packet.

Example 2

Experiments with Varroa mites.

Experiments were conducted during May/June at an apiary in Beltsville, Md. Nine Varroa-infested colonies, each consisting of two-deep Langstroth brood chambers were divided into three groups. Three colonies received a single gel packet (prepared as described in Experiment 1); three colonies were treated with liquid formic acid four times (days 1, 4, 8 and 13); and three colonies served as controls, receiving no treatment. Liquid formic acid treatments consisted of pouring 40 ml of 65% formic acid onto absorbent paper that had been placed across the top bars of the upper brood chamber. After 21 days, formic acid treatments were removed, and all colonies, including controls, were treated with four strips of Apistan® for an additional 21 days in order to give an estimate of the surviving mite population.

Prior to testing, each colony had a small hole drilled in the center of the lower brood chamber to accomodate the insertion of an air monitoring tube (National Dräger, Pittsburgh, Pa.). This arrangement allowed the determination of the concentration of formic acid within the hive at any given time with minimal disturbance.

Sticky boards were placed on the bottom board of all hives during the entire study to monitor mite drop. Efficacy of gel packets and liquid applications were determined by comparing the number of mites collected during the 21-day treatment period to the total number of mites collected (formic acid treatment+Apistan® treatment).

Levels (ppm) of formic acid produced by the gel packets and liquid applications were determined inside colonies every three hours during the first 48 hours of the study (FIG. 1) and every two hours (9 AM to 5 PM) on various days (3, 4, 8, 10 and 15) thereafter (data not shown). With the exception of the initial two readings, levels of formic acid in hives treated with gel packets never dropped below 10 ppm, and in several instances averaged as high as 40–50 ppm. Liquid applications, however, were highest on the day applied and gradually subsided over subsequent days, as shown in FIG. 1. This pattern was consistent with the three additional liquid applications during the course of the study. In most instances, the levels of formic acid in liquid-treated hives remained lower than in hives treated with gel packets. Not surprisingly, there was a general correlation between fluctuations in formic acid levels in treated hives and ambient temperature (FIG. 1). During the warmer parts of the day, levels of formic acid increased, while during cooler evening hours, levels dropped.

The efficacy of the formic acid treatments in controlling Varroa was determined by comparing the number of mites that fell during the formic acid treatment period to the total number of mites that fell, which included the subsequent 21-day treatment with Apistan® (Table III). The efficacy in the three colonies treated with gel packets was 61.3%, 73.2% and 76.3% (average=70.3%). While the efficacy of the liquid treatment was just slightly less (average=61.2%), there was greater variability, with the percent efficacy ranging from 34% to 83.7%. There appeared to be a natural mite drop that averaged about 17.6% in colonies which received no initial treatments.

TABLE III

Efficacy of Gel Packets and Liquid Formic Acid in Controlling *Varroa jacobsoni*.

| | Mite Drop | | | | | | | | |
|---|---|---|---|---|---|---|---|---|---|
| | Controls | | | Gel Packets | | | Liquid | | |
| Colony | A | B | C | D | E | F | G | H | I |
| Treatment totals | 1424 | 4103 | 631 | 3341 | 5129 | 4484 | 3421 | 1353 | 3852 |
| Total mites[1] | 9753 | 23736 | 3000 | 4378 | 8364 | 6125 | 4085 | 3983 | 5848 |
| % Efficacy[2] | (14.6) | (17.3) | (21.0) | 76.3 | 61.3 | 73.2 | 83.7 | 34.0 | 65.9 |
| Average | | (17.6%) | | | 70.26 ± 7.92% | | | 61.2 ± 25.18% | |

[1]Total mites is the number of mites that fell during the 21-day treatment period + number of mites that fell during the subsequent 21-day Apistan ® treatment.
[2]Efficacy is expressed as a ratio of mites that fell during a specific treatment/total mites. Numbers in parentheses indicate "natural" mite fall.

In similar studies conducted in the fall (September/October), the efficiency of the 65% gel packets was 84.4%, 79.4% and 88.0% (average of the 3 replicates=83.9%). Gel packets containing 45% formic acid gel had an average efficiency of 62.5%, and 25% gel packets were less effective, killing 34.4% of Varroa.

Example 3

Tests for Tracheal mites (*A. woodi*).

Worker bees (n=50) infested with tracheal mites were maintained in screened cages (4"×4"×3¼") supplied with sugar syrup. Caged bees were placed on a 6" stand inside fumigation chambers consisting of two-deep Langstroth hive bodies, a bottom board and a screened inner cover. Three cages of bees were exposed to 40 g of a formic acid gel in an open petri dish; three cages were exposed to menthol (50 g, Mann Lake Ltd, Hackensack, Minn.); and three cages remained as untreated controls. All studies were conducted in a greenhouse with temperatures ranging from 72°–94° F. over the eight-day test period. Concentrations of formic acid were measured with monitoring tubes as described in Example 2, and the efficacy of a particular treatment was determined by dissection of live bees and comparing the number of living and dead mites (Eischen et al. 1987. *Amer. Bee J.* vol. 127, pp. 99–101).

Figure 2:
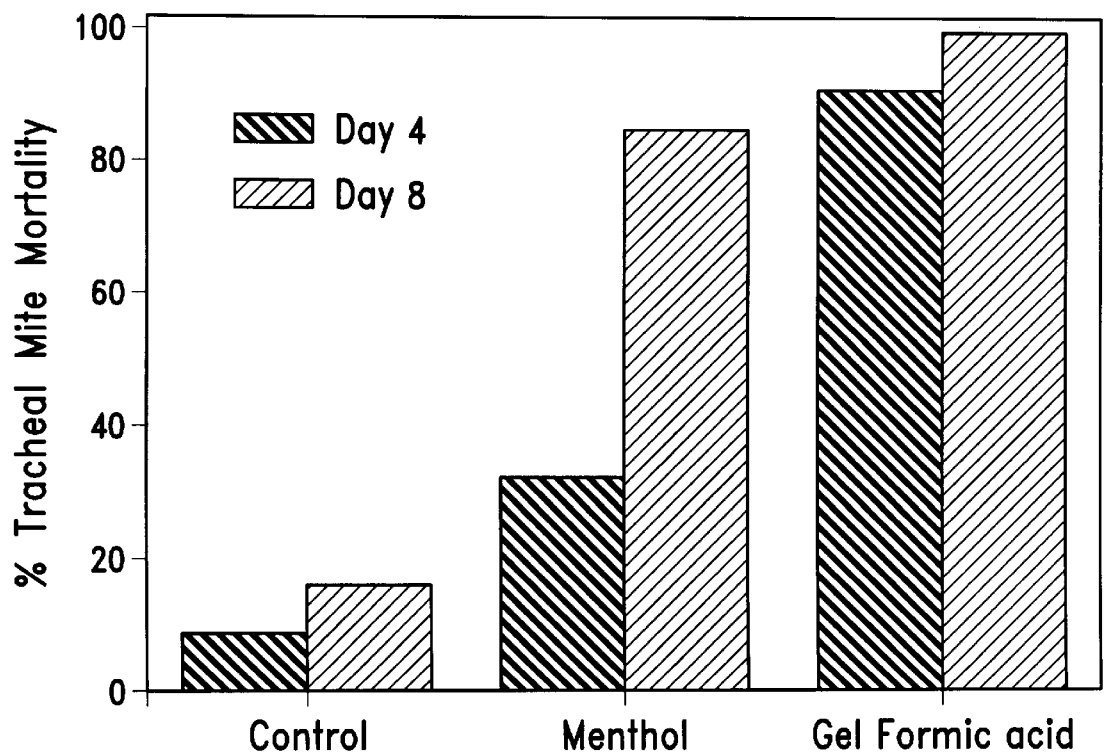
FIG. 2 shows the comparison of tracheal mite (*A. woodi*) mortality (%) in caged bees (three cages/treatment) held in fumigation chambers and treated with either menthol (50 g) or formic acid gel (40 g). Live bees were dissected on day 4 and on day 8 to determine mite mortality. Controls received no treatment.

The ability of the formic acid gel to control the tracheal mite was evident in as few as four days (FIG. 2). Dissections of live bees revealed that mites exposed to the gel suffered 92% mortality at this time, and mortality approached 100% on the eighth day. Levels of formic acid ranged from about 2 ppm–4 ppm over this eight-day period. By comparison, menthol showed only a 32% mortality on day four, and slightly better than 80% mortality on day 8. Tracheal mite mortality in controls receiving no treatment remained well under 20%.

We claim:

1. A gel composition consisting essentially of formic acid in an amount effective for controlling parasitic mites of honey bees and a gelling agent selected from the group consisting of fumed silica and polyacrylic acid, wherein (i) said effective amount of formic acid is at least 60% (v/v) of the gel composition, and (ii) the gel composition is soft but thixotropic and non-slumping, with a consistency ranging from that of a pudding to that of a caulking compound.

2. The gel composition of claim 1, wherein said gelling agent is fumed silica.

3. The gel composition of claim 1, wherein said gelling agent is polyacrylic acid.

4. The gel composition of claim 3, wherein said polyacrylic acid is high molecular weight polyacrylic acid.

5. The gel composition of claim 1, wherein said effective amount of formic acid is about 60% to about 70% (v/v).

6. The gel composition of claim 4, wherein said effective amount of formic acid is about 65% (v/v).

7. A dispenser for the treatment of parasitic mites of honey bees, wherein said dispenser comprises a gel composition consisting essentially of formic acid in an amount effective for control of said parasitic mites and a gelling agent in a container, and wherein (i) said gelling agent is selected from the group consisting of fumed silica and polyacrylic acid, (ii) said effective amount of formic acid is at least 60% (v/v) of the gel composition, (iii) the gel composition is soft but thixotropic and non-slumping, with a consistency ranging from that of a pudding to that of a caulking compound, and (iv) said dispenser allows emission of formic acid vapor.

8. The dispenser of claim 7, wherein said gelling agent is fumed silica.

9. The dispenser of claim 7, wherein said gelling agent is polyacrylic acid.

10. The dispenser of claim 9, wherein said gelling agent is high molecular weight polyacrylic acid.

11. The dispenser of claim 7, wherein said effective amount of formic acid is about 60% to about 70% (v/v).

12. The dispenser of claim 11, wherein said effective amount of formic acid is about 65% (v/v).

13. A method of controlling parasitic mites of honey bees, said method comprising treating said honey bees with a gel composition consisting essentially of formic acid in an amount effective for controlling said parasitic mites and a gelling agent selected from the group consisting of fumed silica and polyacrylic acid, wherein (i) said effective amount of formic acid is at least 60% (v/v) of the gel composition, and (ii) the gel composition is soft but thixotropic and non-slumping, with a consistency ranging from that of a pudding to that of a caulking compound.

14. The method of claim 13, wherein said treating step is carried out by placing said gel composition inside a honey bee hive so that the formic acid vapors are distributed in the hive.

15. The method of claim 13, wherein said parasitic mites of honey bees are *Varroa jacobsoni* or *Acarapis woodi*.

16. The method of claim 13, wherein said parasitic mites of honey bees are *Varroa jacobsoni*.

17. The method of claim 13, wherein said parasitic mites of honey bees are *Acarapis woodi*.

18. The method of claim 13, wherein said gelling agent is fumed silica.

19. The method of claim 13, wherein said gelling agent is polyacrylic acid.

20. The method of claim 19, wherein said polyacrylic acid is high molecular weight polyacrylic acid.

21. The method of claim 13, wherein said effective amount of formic acid is about 60% to about 70% (v/v).

22. The method of claim 21, wherein said effective amount of formic acid is about 65% (v/v).

* * * * *